US012605259B2

(12) United States Patent (10) Patent No.: US 12,605,259 B2
Balint et al. (45) Date of Patent: Apr. 21, 2026

(54) PROSTHETIC SYSTEM, JOINT PROTECTION DEVICE, AND COVER ELEMENT

(71) Applicant: OTTO BOCK HEALTHCARE PRODUCTS GMBH, Vienna (AT)

(72) Inventors: Marton Balint, Vienna (AT); Johannes Bischof, Wiener Neustadt (AT); Walter Lunzer, Vienna (AT); Thomas Ecker-Wessely, Eichgraben (AT); Alice Scherb, Stockerau (AT); Sonja Wagner, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 740 days.

(21) Appl. No.: 17/919,220

(22) PCT Filed: Apr. 15, 2021

(86) PCT No.: PCT/EP2021/059785
§ 371 (c)(1),
(2) Date: Oct. 14, 2022

(87) PCT Pub. No.: WO2021/209550
PCT Pub. Date: Oct. 21, 2021

(65) Prior Publication Data
US 2023/0157850 A1 May 25, 2023

(30) Foreign Application Priority Data
Apr. 16, 2020 (DE) .................... 10 2020 110 402.2

(51) Int. Cl.
A61F 2/64 (2006.01)
A61F 2/58 (2006.01)
A61F 2/50 (2006.01)

(52) U.S. Cl.
CPC ................ *A61F 2/64* (2013.01); *A61F 2/582* (2013.01); *A61F 2002/5001* (2013.01); *A61F 2002/5039* (2013.01)

(58) Field of Classification Search
CPC .... A61F 2/64; A61F 2/582; A61F 2002/5001; A61F 2002/5039
See application file for complete search history.

(56) References Cited

U.S. PATENT DOCUMENTS

| 2,078,595 A | 4/1937 | Barghausen | |
| 9,889,024 B2 * | 2/2018 | Sawatzki | ................... A61F 2/50 |

(Continued)

FOREIGN PATENT DOCUMENTS

| DE | 19627994 A1 | 1/1997 |
| DE | 102012009757 A1 | 12/2013 |

(Continued)

OTHER PUBLICATIONS

"International Search Report and Written Opinion of the International Searching Authority," issued in connection with Int'l Appl. No. PCT/EP2021/059785 dated Jul. 19, 2021 (24 pages).

*Primary Examiner* — Bruce E Snow
(74) *Attorney, Agent, or Firm* — HOLLAND & HART LLP

(57) ABSTRACT

A prosthetic system with a prosthesis, which has two prosthetic parts that are pivotally connected together about a joint axis via a prosthetic joint with a joint upper part and with a joint lower part, and a cover element, which at least partly covers a gap between the two prosthetic parts or between one prosthetic part and the joint lower part. The cover element is pivotally mounted about a pivot axis on one prosthetic part, a component of a cosmetic prosthetic element, said component being secured to one prosthetic part or one joint part or the prosthetic joint and is coupled to the joint upper part of the prosthetic joint via at least one (Continued)

coupling element in a form- and/or force-fitting manner such that a pivotal movement of the prosthetic parts about the joint axis leads to a simultaneous pivotal movement of the cover element about the pivot axis.

13 Claims, 5 Drawing Sheets

(56)                    References Cited

U.S. PATENT DOCUMENTS

2002/0077703 A1*   6/2002  Johnson .................... A61F 2/78
                                                              623/27
2015/0359643 A1    12/2015  Terleski et al.
2020/0038203 A1*    2/2020  Piller ...................... A61F 2/582

FOREIGN PATENT DOCUMENTS

DE       102016103743  B3     5/2017
DE       102016119001  A1     4/2018
JP          06-189992  A      7/1994
WO        2017/149033  A1     9/2017

* cited by examiner

PROSTHETIC SYSTEM, JOINT PROTECTION DEVICE, AND COVER ELEMENT

CROSS REFERENCE TO RELATED APPLICATIONS

This is a national phase application of International Application No. PCT/EP2021/059785, filed 15 Apr. 2021, which claims the benefit of German Patent Application No. 10 2020 110 402.2, filed 16 Apr. 2020, the disclosures of which are incorporated herein, in their entireties, by this reference.

TECHNICAL FIELD

The invention relates to a prosthesis system having a prosthesis, in particular a prosthesis of the lower or upper extremity, which has two prosthesis parts connected to each other pivotably about a joint axis via a prosthesis joint with a joint upper part and a joint lower part, and having a cover element which at least partially covers a gap between the two prosthesis parts or between one prosthesis part, in particular a proximal prosthesis part, and the joint lower part.

BACKGROUND

The prosthesis is preferably a prosthesis of the lower or upper extremity and is arranged on a thigh stump or an upper arm stump of a patient. For this purpose, the prosthesis has a proximal prosthesis part, which is secured to the stump, and a distal prosthesis part, which is connected to the proximal prosthesis part pivotably about the joint axis via the prosthesis joint. The distal prosthesis part, in particular in combination with the joint lower part, thus replaces the lower leg or forearm of the patient. The prosthesis joint is accordingly a prosthetic knee joint or a prosthetic elbow joint.

Such prostheses usually have, particularly in the flexed state, a gap between the proximal prosthesis part and the distal prosthesis part or between the proximal prosthesis part and the joint lower part, and they also have, in any state, a gap between the joint upper part and the joint lower part, which gaps can be of different sizes depending on the angle of the proximal prosthesis part to the distal prosthesis part. The gap is thus usually of minimal size in a maximally extended position, i.e. with the leg or arm fully extended. As flexion increases, the gap grows larger. This has the effect that the prosthesis joint is exposed to environmental influences, with the additional risk that an item of clothing that covers the prosthesis will become caught in the gap during an extension movement.

Moreover, the human knee in particular has a characteristic shape that has to be imitated in order to obtain a prosthesis that is as inconspicuous as possible.

For this reason, it is known to provide a cover element which at least partially covers the gap.

For example, DE 10 2016 103 743 B3 discloses a prosthesis cosmetic with a plurality of clasp elements which are interconnected in an articulated manner and coupled to one another via a tension element. The prosthesis cosmetic is fixed with one end on the distal prosthesis component and with one end on the proximal prosthesis component of the prosthesis. The clasp elements partially cover the gap created between the proximal and the distal prosthesis component.

DE 10 2012 009 757 A1 relates to a cover for a prosthesis device, in particular a prosthetic leg, the cover at least partially covering the joint device between a first prosthesis part and a second prosthesis part in the pivoted state. There is still a gap present. However, a disadvantage is that the cover is structurally very complex and cannot be easily removed or fitted by a prosthesis user.

SUMMARY

The object of the invention is to remedy the disadvantages of the prior art.

The invention achieves this object with a prosthesis system having the features of the main claim. Advantageous embodiments and developments of the invention are set forth in the subclaims, the description and the figures.

In the prosthesis system according to the invention having a prosthesis, in particular a prosthesis of the lower or upper extremity, which has two prosthesis parts connected to each other pivotably about a joint axis via a prosthesis joint with a joint upper part and a joint lower part, and having a cover element which at least partially covers a gap between the two prosthesis parts or between one prosthesis part and the joint lower part, provision is made that the cover element is mounted pivotably about a pivot axis on a prosthesis part, on a component of a prosthesis cosmetic secured to a prosthesis part or joint part, or on the prosthesis joint and is coupled to the joint upper part of the prosthesis joint via at least one coupling element in a form-fitting and/or force-fitting manner, such that a pivoting movement of the prosthesis parts about the joint axis leads to a simultaneous pivoting movement of the cover element about the pivot axis.

According to a preferred embodiment, the cover element is mounted pivotably about the pivot axis on the distal prosthesis part, on a prosthesis cosmetic secured to the distal prosthesis part or the joint lower part, or on the joint lower part of the prosthesis joint. However, within the scope of the invention, it is likewise possible that the cover element is arranged on the proximal prosthesis part, or on a component of a prosthesis cosmetic secured to the proximal prosthesis part or the joint upper part, or on the joint upper part.

A prosthesis cosmetic is also understood in particular to mean a prosthesis protector or, for example, also a shape compensation element. The various embodiments of a prosthesis cosmetic serve in particular to give the prosthesis a more physiological appearance and/or to protect the constituent parts of the prosthesis from environmental influences such as moisture or dirt.

The cover element is preferably arranged on the physical joint axis of the prosthesis joint, in particular plugged onto it, clipped onto it or latched onto it. The physical joint axis can be configured as a bolt, pin or the like, on which the cover element is mounted. According to a further preferred embodiment, the cover element is arranged on the joint lower part of the prosthesis joint.

The joint upper part is usually the structural part of the prosthesis joint on which the proximal prosthesis part is secured. In this case, the cover element is arranged, for example, on the joint lower part, or a component of the prosthesis cosmetic of the joint lower part. However, it is likewise possible for the distal prosthesis part to be secured on the joint upper part.

The prosthesis joint usually consists of a joint upper part, which is also designated as the joint head, and a joint lower part, which is also designated as the joint frame. The joint upper part and the joint lower part are pivotably connected to each other via a physical joint axis. This physical joint axis can be part of the joint upper part or joint lower part or can be designed as a separate structural part. The joint lower part has, for example, a fork-shaped frame with sockets in which the physical joint axis with the joint upper part arranged thereon is mounted. The joint upper part preferably has a pyramid adapter or a screw thread for attachment of a prosthesis part, in particular of the proximal prosthesis part.

It is possible for the cover element to be directly mounted pivotably on the prosthesis part, on a component of the prosthesis cosmetic or on the prosthesis joint. In this case, the cover element is mounted on the prosthesis part, the prosthesis cosmetic or the prosthesis joint, for example by means of form-fit and/or force-fit elements, via corresponding elements, for example recesses. However, it is likewise possible for the cover element to be mounted on said structural parts via further elements. This will be explained in more detail in the following.

The cover element is coupled to the joint upper part in a form-fitting and/or force-fitting manner via at least one coupling element, that is to say in particular is fixed relative to the joint upper part. When the joint upper part executes a pivoting movement about the joint axis relative to the joint lower part, the cover element follows the joint upper part through the coupling by accordingly pivoting about the pivot axis of the cover element. Since the joint upper part and the joint lower part are each connected to a prosthesis part, a pivoting movement of the prosthesis parts about the joint axis accordingly leads to a simultaneous pivoting movement of the cover element.

As the pivoting movement of the cover element follows the pivoting movement of a prosthesis part, the gap, increasing in size during a flexion movement, between the two prosthesis parts or between the prosthesis part and the joint lower joint part is at least partially covered by the cover element. The dimensions of the cover element determine the degree to which the cover element covers the gap. At the same time, this of course depends on the angle between the prosthesis parts and on the size of the gap, which is dependent on the angle.

In the case of prosthetic arms or legs, the distal prosthesis part is usually pivotable relative to the prosthesis part from an angle of 0°, i.e. maximum extension, up to an angle of 120° to 160°, in particular up to an angle of about 135°, i.e. maximum flexion, and vice versa.

The cover element is preferably dimensioned in such a way that it covers the gap at pivoting angles from 0° to 45°, preferably from 0° to 50°, in particular from 0° to 90°. This is to be understood as meaning that, in the case of the prosthetic leg, the cover element covers the gap ventrally, and, in the case of the prosthetic arm, on the side opposite the elbow, over the stated angle range.

In one variant, the cover element is part of a multi-part joint protection device which is secured on the prosthesis part, on a component of the prosthesis cosmetic or on the prosthesis joint and has a visor on which the cover element is pivotably mounted about the pivot axis. The joint protection device is preferably secured on the joint lower part of the prosthesis joint or on a component of the prosthesis cosmetic that is mounted thereon.

In this embodiment, the cover element is not necessarily mounted directly pivotably on the prosthesis part of the prosthesis cosmetic or on the prosthesis joint. This can also be effected via the visor of the joint protection device or in combination with the visor. The visor and cover element preferably have two physical axes which are identical for the visor and cover element. In this embodiment, the visor and the cover element are connected to each other via these physical axes. For this purpose, both have sockets, for example, into which axles are inserted. These axles are preferably constructed in two parts and screwed together. The axles preferably have connecting structures, such that they simultaneously function as attachment elements for joining to a carrier, to a component of the prosthesis cosmetic, to a prosthesis part and/or to the prosthesis joint, in particular to the joint lower part of the prosthesis joint.

The visor and the cover element preferably form a structural unit and, as a module, are preferably not separable from each other without being destroyed, i.e. without, for example, loosening of the screwed connection of the axles.

In a further development, provision is made that the joint protection device moreover has a carrier, which is in particular a component of the prosthesis cosmetic on which the cover element and/or the visor are/is secured. In other words, the joint protection device in this embodiment is designed in at least three parts, namely with the carrier, the visor and the cover element. The cover element is pivotably mounted on the visor, for example, and the visor itself is secured on the carrier. In the preferred embodiment, in which cover element and visor share the same physical axes, cover element and visor are mounted pivotably on the carrier in a correspondingly combined manner. In this case, the joint protection device is secured on the prosthesis part or on the prosthesis joint by means of the carrier.

The visor, with the cover element arranged thereon, preferably has form-fit and/or force-fit elements for securing the visor on the carrier. For this purpose, the carrier preferably has connection elements.

The visor and the cover element can be formed from an elastic material, in particular a plastic, composite material or metal. In one embodiment, the visor and the cover element have a clasp-shaped design. On an inner side of the visor facing toward the carrier, the visor then preferably has form-fit elements which are clipped or inserted into corresponding recesses in the carrier. For this purpose, the visor is widened counter to the restoring force of the elastic material and moved over the carrier. The form-fit elements are then introduced into the corresponding recesses by the restoring force, and the visor is secured on the carrier. They may also have to be pressed manually into the corresponding recesses.

The cover element, the visor or the carrier preferably has form-fit and force-fit elements via which the joint protection device is secured on the prosthesis part, on the prosthesis cosmetic or on the prosthesis joint.

If the joint protection device does not have a carrier, then the visor preferably has form-fit and/or force-fit elements in order to secure the joint protection device on the prosthesis part, on the prosthesis cosmetic or on the prosthesis joint. If the joint protection device has a carrier, then the form-fit and/or force-fit elements are arranged on the carrier for connection to them.

The form-fit and/or force-fit elements can be, for example, fastening means for a bayonet connection. For this purpose, the prosthesis part, the prosthesis cosmetic or the prosthesis joint then has corresponding mating elements. In addition, it is likewise possible that the form-fit and/or force-fit elements are designed as magnets, or that the corresponding attachment means on the prosthesis part of the prosthesis cosmetic or on the prosthesis joint are designed as magnets.

In one embodiment, the joint protection device has a clasp-shaped design and is secured on the prosthesis part, on the prosthesis cosmetic or on the prosthesis joint via a snap-fit connection in particular.

In a further development, not only do the cover element and the visor have a clasp-shaped design, but the carrier also has a clasp-like structure, namely such that it partially engages around the prosthesis part, the prosthesis cosmetic or the prosthesis joint and has corresponding attachment means for providing a snap-fit connection. For this purpose, the carrier has, for example, recesses that are clamped onto corresponding projections. For this purpose, the carrier is preferably made of an elastic material, such that it can be widened counter to a restoring force of the material. The carrier is then positioned over the corresponding elevations. The carrier is returned to its original shape by the restoring force and is then secured on the prosthesis part, on the prosthesis cosmetic or on the prosthesis joint.

In one embodiment, the elevations and the recesses are dimensioned, in particular designed asymmetrically, such that a rotation of the carrier relative to the structural part is not possible without deformation.

The visor and/or the carrier can at least partially project over the gap between the two prosthesis parts.

This means that, irrespective of a pivoting angle between the two prosthesis parts, the gap is always covered to a certain extent by the visor and/or the carrier. In one embodiment, the cover element projects over the gap in such a way that the latter is completely covered in the state of maximum extension, that is to say in the state in which the gap is smallest. Complete coverage is understood to mean, in particular, that the gap is covered ventrally in the case of a prosthetic leg and is covered opposite the elbow in the case of a prosthetic arm.

The at least partial projection over the gap makes it possible to cover a greater angle range by means of the cover element and the visor and/or carrier. The mechanics of the joint protection device are preferably designed in such a way that the visor and the cover element pivot jointly up to a certain pivoting angle, for example of 75°. Then, upon further pivoting, the visor remains stationary and only the cover element continues to pivot, in particular along with the proximal prosthesis part. The visor preferably remains stationary in such a way that its orientation relative to the joint lower part does not change in the case of a further pivoting, that is to say a further increase of the pivoting angle.

It is possible, but not necessary, for a gap to be formed between the visor and the joint lower part when the visor has stopped. In one embodiment of the invention, cover element and visor completely cover the gap up to a pivoting angle of approximately 50°. Once this pivoting angle is reached, a gap forms between the visor and the joint lower part. This increases until the visor stops, for example at a pivoting angle of 75°. This makes it possible, for example, to provide sufficient coverage over a greater angle range without the joint protection device having to be dimensioned in such a way that the gap is completely covered irrespective of the pivoting angle. Tests by the applicant have shown that formation of a slight gap, as in the embodiment mentioned, may be acceptable.

In one embodiment, the visor is secured on the carrier, on the prosthesis part, on the prosthesis cosmetic or on the prosthesis joint so as to be pivotable about a pivot axis, the pivot axes of the visor and of the cover element preferably coinciding.

If the joint protection device has a carrier, the visor is secured pivotably on this carrier. If the joint protection device does not have a carrier, the visor is mounted pivotably on the prosthesis part, on the prosthesis cosmetic or on the prosthesis joint. The cover element is in turn mounted pivotably on the visor, or visor and cover element share the physical axes, which is the subject of a preferred embodiment.

The fact that the pivot axes of the visor and of the cover element coincide is preferably understood to mean that they are actually identical. When coincident axes are referred to in this description, this also includes, in particular, slight deviations of the axes from one another, which can be compensated for example by the elasticity of the material and/or are caused by manufacturing tolerances.

In one embodiment, the visor and the cover element are additionally coupled to each other via at least one driver, or the at least one driver is arranged on the cover element and, by pivoting of the cover element relative to the visor, can be brought into engagement with a corresponding element of the visor.

This embodiment, in which both the visor and the cover element are pivotably mounted, ensures that the gap between the prosthesis parts can be covered over the greatest possible angle range, preferably over the entire flexion angle of the prosthesis joint.

The driver is, for example, a spring-loaded catch that can clip in and out.

In one embodiment, the cover element has a projection which is slidably mounted in a corresponding groove of the visor element. During a pivoting movement of the cover element, the projection slides in the groove until it rests against a stop of the visor and engages with the latter. A further pivoting movement of the cover element then leads to the visor being entrained and thus to a simultaneous pivoting movement of the visor.

In this way it is possible, for example, for the gap to be completely covered by the cover element up to a pivoting angle of 90°. However, further pivoting of the cover element would lead to the gap being exposed again. However, by means of the driver and of the visor coupled to the cover element, this gap is not exposed, and instead the cover element and visor now jointly cover the gap such that, for example, the gap remains covered, by cover element and visor together, up to a pivoting angle of 120° or 135°.

The pivot axis of the cover element and the joint axis of the prosthesis joint preferably coincide. This means that the axis about which the prosthesis parts are pivoted relative to one another is identical to the axis about which the cover element is pivoted. These are not the physical axes, but the imaginary axes of rotation. This ensures that no tension or deformation occurs when the cover element and the prosthesis parts are pivoted at the same time, as is provided according to the invention.

In one embodiment in which both the visor and the cover element are pivotably mounted, the joint axis and the pivot axes of the visor and of the cover element advantageously coincide. This ensures that the pivoting leads to little or no deformation at all.

For simpler manufacture, the coupling element is designed in one piece with the cover element, in particular in the form of a web, a clasp or a clip.

In the case of a prosthetic leg, the at least one coupling element preferably extends in the dorsal direction. In the case of a prosthetic arm, the at least one coupling element preferably extends in the direction of the elbow.

The coupling element is designed to couple to the joint upper part. In the simplest case, the at least one coupling element is secured directly on the joint upper part, for example by clamping or latching. However, it is likewise possible that the at least one coupling element is not coupled directly to the joint upper part, but is instead clamped, for example, between the joint upper part and a prosthesis part, in particular the proximal prosthesis part. In this case too, the at least one coupling element is coupled to the joint upper part within the meaning of the invention.

The at least one coupling element is preferably latched or clamped onto the joint upper part. In one embodiment, the at least one coupling element is designed as a clasp or clamp which at least partially engages around the joint upper part.

In one embodiment, the at least one coupling element is designed as a web which in particular has a projection which engages under the joint upper part or is clamped between the joint upper part and a prosthesis part, in particular the proximal prosthesis part.

In one embodiment, the proximal prosthesis part is secured on the joint upper part, in particular via a pyramid adapter, and the coupling element is clamped in the form of a web between the joint upper part and the proximal prosthesis part.

According to a further aspect, the invention relates to a joint protection device for such a prosthesis.

According to a further aspect, the invention relates to a cover element for such a prosthesis or for such a joint protection device, wherein the cover element can have form-fit and/or force-fit elements by means of which it can be secured on the prosthesis part, on the prosthesis cosmetic or the prosthesis joint.

BRIEF DESCRIPTION OF THE DRAWINGS

The invention is explained in more detail below with reference to the accompanying figures, in which.

DETAILED DESCRIPTION

Figure 1:
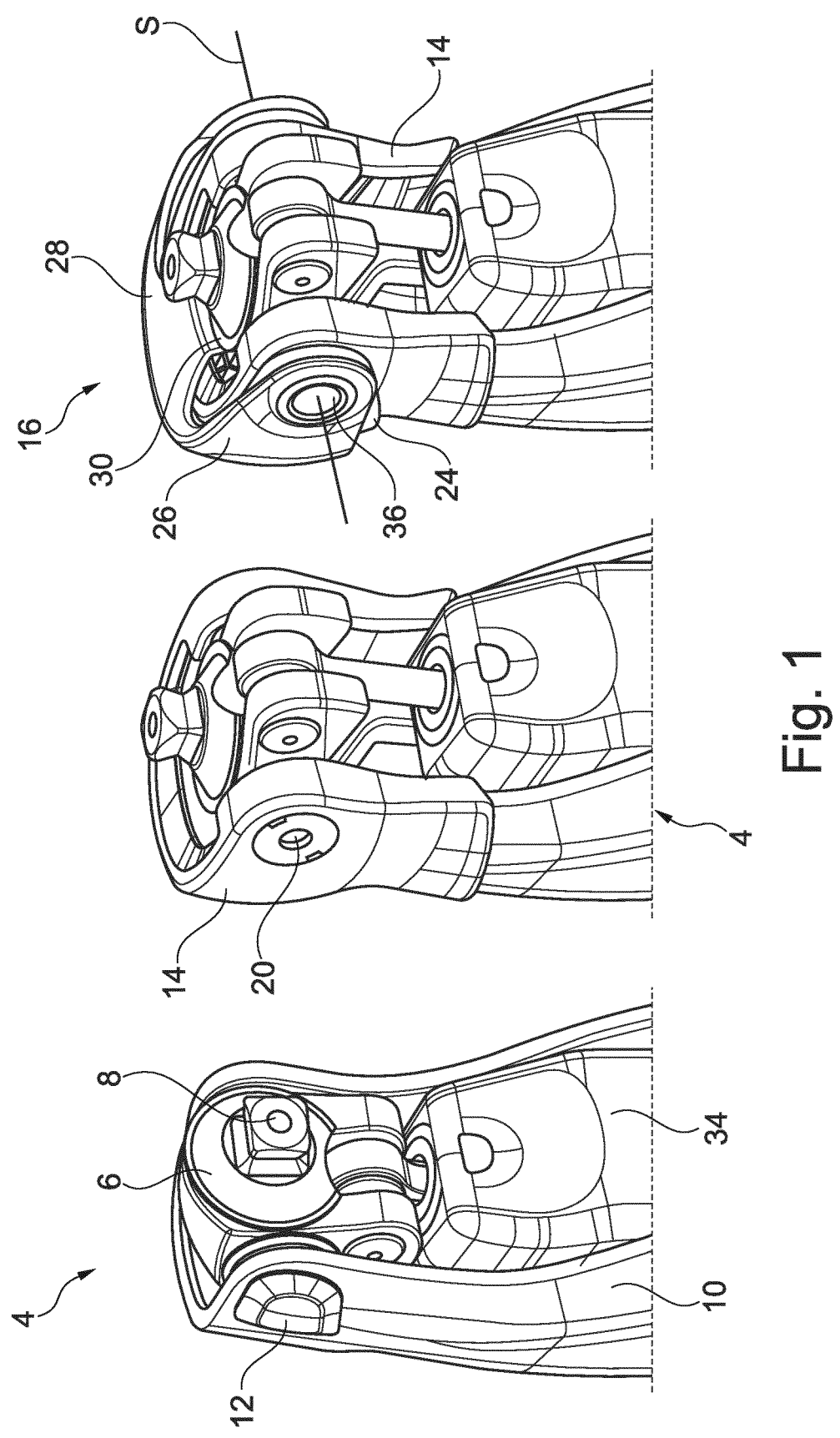
FIG. 1 shows a prosthesis joint with a joint protection device in three different states.

FIG. 1 shows a prosthesis joint 4 of a prosthesis for a lower extremity. In the present case, the prosthesis joint 4 is the prosthetic knee joint of a prosthetic leg. The prosthesis joint 4 has a joint upper part 6. A pyramid adapter 8 for attachment of a proximal prosthesis part, for example a prosthesis socket of the prosthetic leg, is arranged on the joint upper part 6, the latter also being designated as the joint head. The prosthesis joint 4 also has a joint lower part 10. The joint lower part 10 and the joint upper part 6 are pivotable relative to each other about a joint axis. The distal prosthesis part, for example a lower-leg tube or a prosthetic foot, is secured on the joint lower part 10.

In the picture on the left, the joint upper part 6 is shown pivoted relative to the distal prosthesis part and thus at the same time relative to the joint lower joint part 10. This is the state of a flexion about the joint axis of approximately 90°. The prosthesis part can have a prosthesis cosmetic.

The joint lower part 10 has two projections 12, which are not rotationally symmetrical about the joint axis; only one of the projections 12 can be seen in the picture on the left in FIG. 1. If the distal prosthesis part has a prosthesis cosmetic, the latter can use these projections 12 for a form-fit hold on the prosthesis joint 4.

In the middle picture, the prosthesis joint 4 is shown with a maximally extended joint upper part 6. In this picture, a carrier 14 of a joint protection device 16 is arranged on the prosthesis joint 4. The carrier 14 has structures 18 (shown first in FIG. 3) which correspond to the projections 12.

The carrier 14 is secured releasably on the prosthesis joint 4 and in particular on the joint lower part 10 via the projections 12 and corresponding structures 18. On account of the non-rotationally symmetrical shape of the projections 12 and of the correspondingly configured structures 18 of the carrier 14, the carrier 14 is secured relative to the prosthesis joint 4 and the joint lower part 10 and is not pivotable relative thereto.

The carrier 14 has two connection elements 20, of which only one can be seen in the middle picture in FIG. 1. These correspond to attachment elements 22 (shown in FIG. 2) of the joint protection device 16. The attachment elements 22 are designed as form-fit elements that correspond to the connection elements 20 of the carrier 14. This creates a releasable connection between the joint protection device and the carrier 14. The attachment elements 22 are preferably at the same time the physical axes of cover element and visor.

In the picture on the right in FIG. 1, the prosthesis joint 4 is shown with the joint protection device 16 arranged completely thereon. The joint protection device 16 has the carrier 14, a visor 24 and a cover element 26.

The cover element 26 has a coupling element 28, which in the present case is designed in one piece with the cover element 26.

The coupling element 28 is designed in this embodiment as a web that extends dorsally or to the rear. In addition, the coupling element 28 has a portion 30 that extends distally or downward. This portion 30 has a contact face 32 (not shown in FIG. 1) with which the coupling element 28 bears on the joint upper part 6. The portion 30 has a curvature corresponding to the curvature of the joint upper part 6.

On account of the geometry of the coupling element 28 as shown, the latter not only bears on the joint upper part 6 but also engages with the latter in the manner of a snap-fit mechanism. In this way, the cover element 26 is coupled to the joint upper part 6 via the coupling element 28. Alternatively or in addition, it is possible that the coupling element 28 is clamped between the joint upper part 6 and a proximal prosthesis part (not shown in FIG. 1) attached to the pyramid adapter 8.

In addition, the prosthesis joint from FIG. 1 has a damping device 34, which is coupled to the two joint parts 6, 10.

If the prosthesis joint 4 executes a pivoting movement from the position shown in the middle and right pictures to the position shown in the left picture, the cover element 26 performs a simultaneous pivoting movement about the pivot axis S on account of the coupling to the joint upper part 6 via the coupling element 28. In this way, the gap existing between the joint lower part 10 or a distal prosthesis component (not shown) and the proximal prosthesis part (not shown), and increasing in size in the course of the pivoting movement, is at least partially, in particular completely, covered ventrally.

The attachment elements 22 can be secured on the carrier 14 via the connection elements 20 such that it cannot execute any movement relative thereto. The cover element 26 and the visor 24 can still be made pivotable about the attachment elements 22. However, in a further embodiment, it is also possible for the visor 24 to be arranged pivotably on the carrier 14 about a pivot axis via the attachment elements 22 and the connection elements 20. In the embodiment shown in FIG. 1, the pivot axis of the visor 24 and pivot axis S of the cover element 26 coincide. Their physical axes are preferably also identical. At the same time, these pivot axes also coincide with the joint axis of the prosthesis joint 4.

The cover element 26 preferably has a driver 100 which is either permanently coupled to the visor 24 or can be brought into engagement with a corresponding element of the visor 24. By means of the at least one driver 100, it is possible for the visor 24 to be driven from the cover element 26 by up to a certain degree of pivoting relative to the joint lower part. In another embodiment, the at least one driver 100 makes it possible that the cover element 26, preferably starting from a certain degree of pivoting relative to the joint lower part 10, also brings about a pivoting of the visor 24 relative to the joint lower part 10 or the distal prosthesis component. This is particularly useful when the prosthesis joint 4 permits a pivoting in which the resulting gap between the proximal prosthesis part and the joint lower part 10 is no longer able to be covered by the cover element 26 alone. The additional pivoting of the visor 24 thus ensures additional covering of the resulting gap, and therefore shielding of the prosthesis joint 4 from environmental influences.

Figure 2:
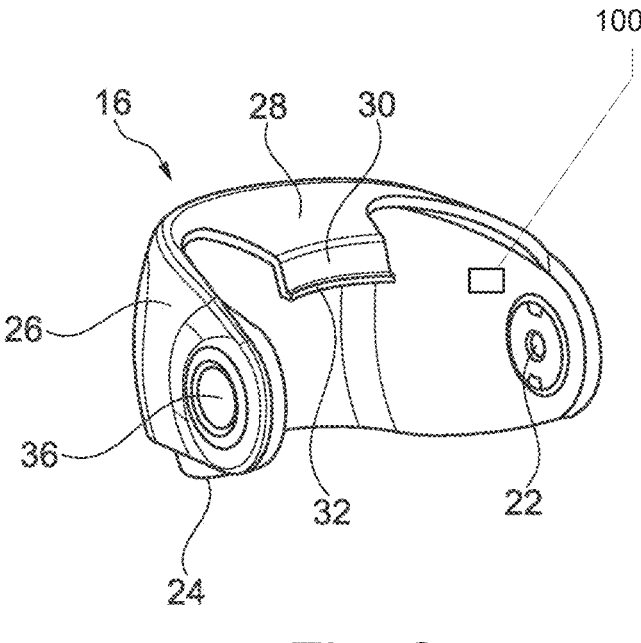
FIG. 2 shows a first embodiment of a joint protection device with cover element and visor.

FIG. 2 shows the combination of a cover element 26 and a visor 24. These already form an independent embodiment of a joint protection device 16 within the meaning of the present invention. However, the joint protection device 16 preferably moreover has a carrier 14 on which the visor 24 and thus also the cover element 26 are arranged.

The visor 24 and the cover element 26 are preferably connected to each other in such a way that they are not separable without being destroyed. For this purpose, the attachment elements 22 are preferably at the same time the physical axes about which cover element and visor are pivotable. These attachment elements 22 are constructed in two parts and screwed together. Without release of this screwed connection, cover element 26 and visor 24 cannot then be separated from each other without being destroyed. The visor 24 and cover element 26 shown in FIG. 2 correspond to the embodiment from FIG. 1. In addition, FIG. 2 shows in more detail the attachment elements 22 for joining to the connection elements 20 of the carrier 14.

The cover element 26 is mounted pivotably on the visor 24 about two joints 36. These joints 36 can at the same time be the attachment elements 22. As has already been mentioned with respect to FIG. 1, the cover element 26 has a coupling element 28. The latter has a distally extending portion 30, and also a contact face 32 for the joint upper part 6 of a prosthesis joint 4.

Figure 3:
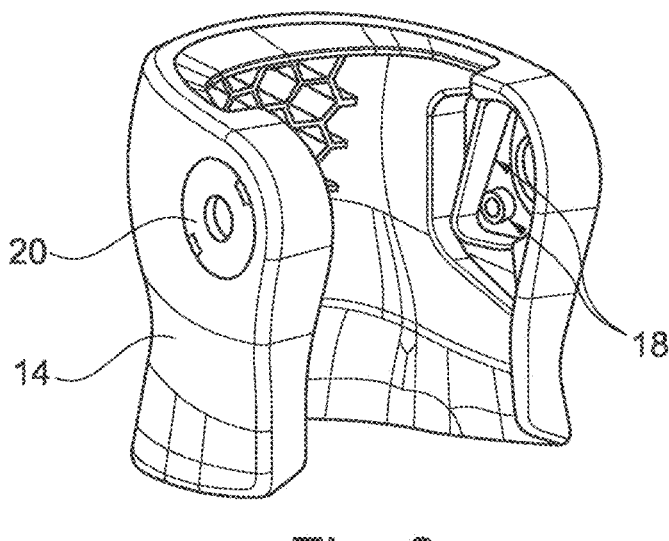
FIG. 3 shows an embodiment of a carrier for a joint protection device.

FIG. 3 shows the carrier 14 of a joint protection device 16. The carrier 14 from FIG. 3 corresponds to the embodiment from FIG. 1.

FIG. 3 reveals one of the two structures 18 via which carrier 14 can be secured on a prosthesis cosmetic or on the prosthesis joint 4, in particular on the joint lower part 10 of the prosthesis joint 4. In the embodiment shown in FIG. 1, the carrier 14 is secured on the joint lower part 10 via the structures 18 and the corresponding projections 12.

The carrier 14 is preferably made of an elastic plastic, such that the carrier 14 can be widened slightly in order to be placed on the prosthesis joint 4, in particular on the joint lower part 10, and the restoring force of the material brings the carrier 14 back to its original shape. It is thus possible for the carrier 14 to be clamped on particularly easily, for example on the prosthesis joint 4, in particular on the joint lower part 10.

Figure 4:
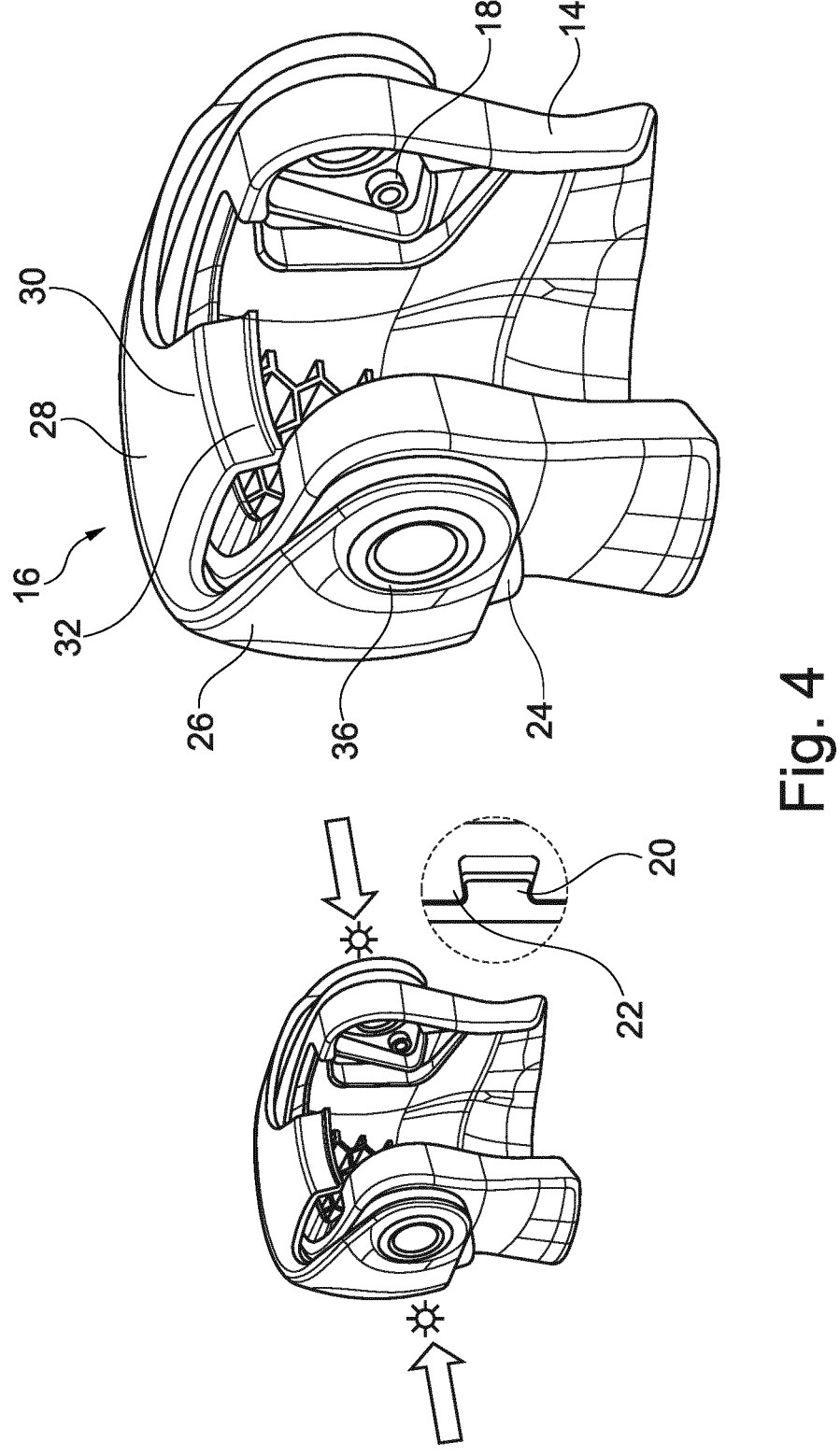
FIG. 4 shows an embodiment of a joint protection device with carrier, visor and cover element.

FIG. 4 shows an embodiment of the joint protection device 16 with carrier 14, visor 24 and cover element 26. The carrier 14 corresponds to the embodiment from FIG. 3, and the combination of visor 24 and cover element 26 corresponds to the embodiment from FIG. 2. FIG. 4 shows schematically how the visor 24 is secured on the carrier 14 or on a component of the prosthesis cosmetic.

The visor 24 and the cover element 26 have a clasp-shaped design and are made of an elastic material, in particular a plastic. Through widening of the joint protection device 16, the latter can be easily placed onto the carrier 14 or a component of the prosthesis cosmetic, such that the attachment elements 22 of the joint protection device 16 and the connection elements 20 of the carrier 14 are made congruent. These attachment elements 22, designed as form-fit elements, then simply have to be clamped into place by pressing them into the connection elements 20. This is indicated by the arrows.

Figure 5:
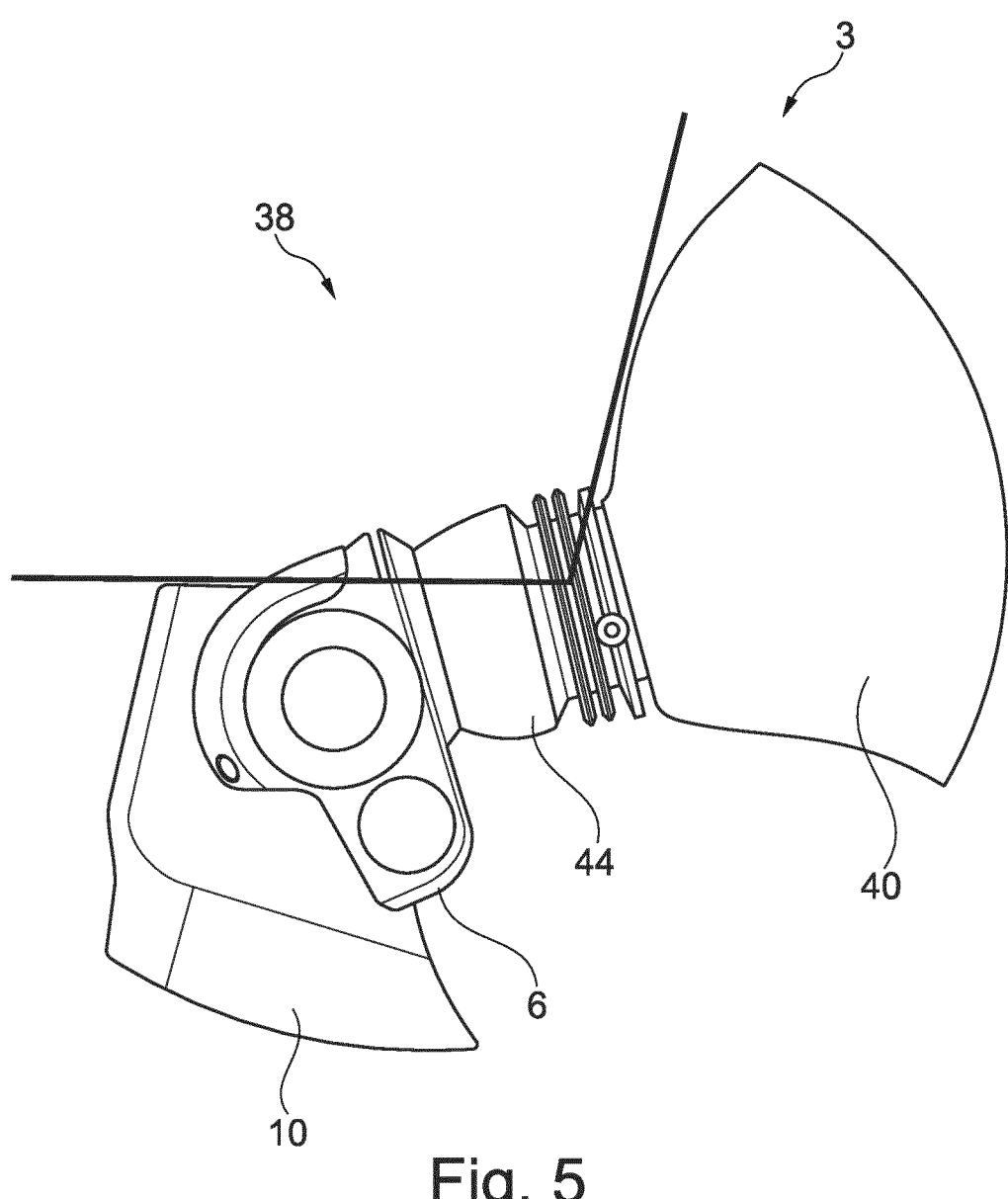
FIG. 5 shows a section through a part of a prosthesis in an embodiment of the prosthesis system.

FIG. 5 shows a section through a part of a prosthesis 3 of a prosthesis system 2 in a flexed state, in which the gap 38 between the proximal prosthesis part 40 and the joint lower part 10 is clearly illustrated. For the sake of clarity, no cover element 26 or joint protection device 16 is shown. A distal prosthesis part 42 (not shown in the detail), for example a lower-leg tube or a foot, is secured on the joint lower part 10. The proximal prosthesis part 40 is secured on the joint upper part 6 via an adapter 44.

Figure 6:
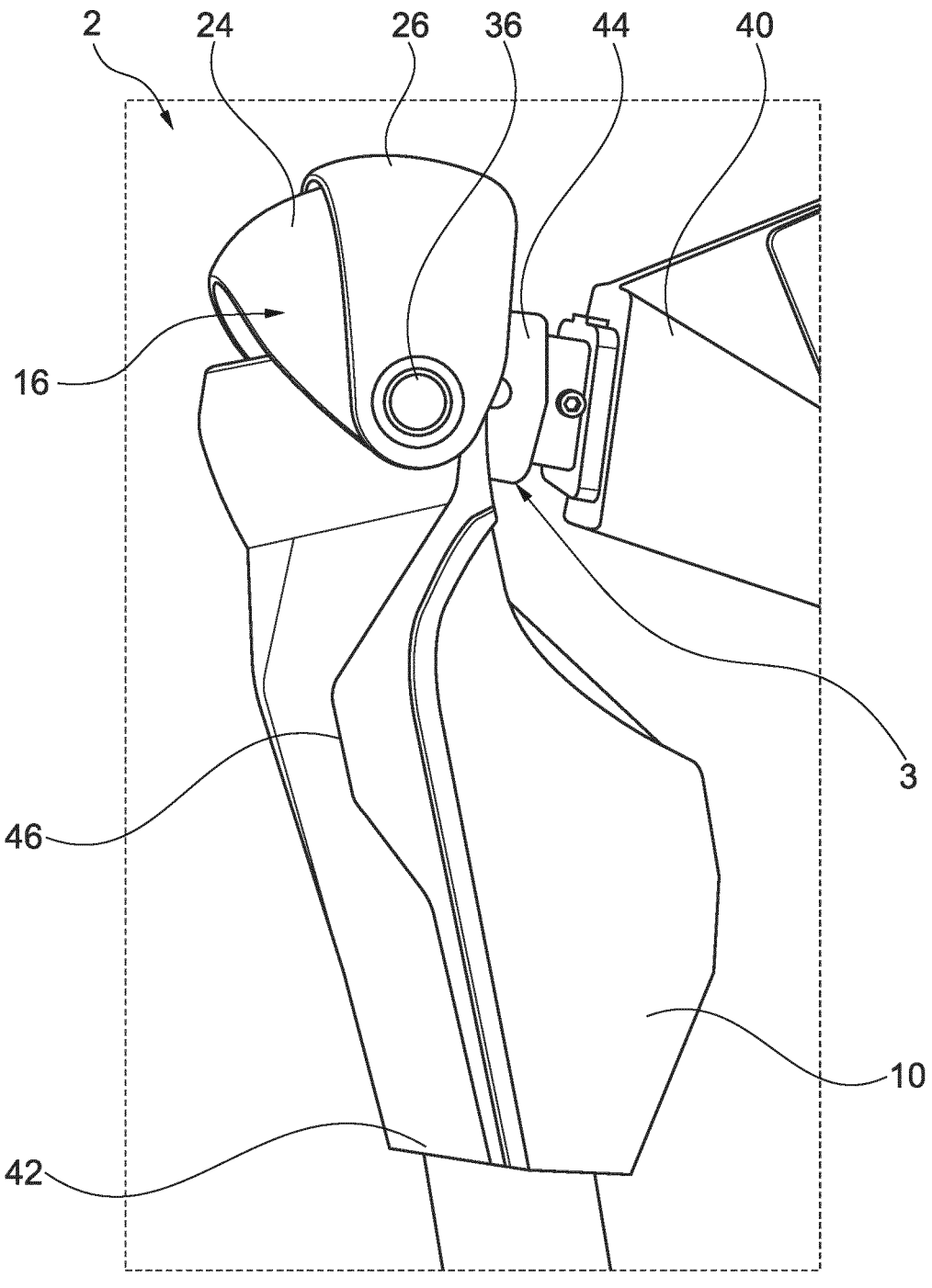
FIG. 6 shows a detail of an embodiment of the prosthesis system.

FIG. 6 shows a detail of an embodiment of the prosthesis system 2 with the prosthesis 3 and the cover element 26, where the cover element 26 is part of a joint protection device 16. The joint protection device 16 moreover has a visor 24. By way of joints 36, which at the same time are attachment elements 22, the joint protection device 16 is mounted pivotably on a prosthesis cosmetic 46, which is secured to the joint lower part 10 and in the present case is designed as a protector. The joints 36 are the physical axes, namely axle bolts or axle journals, about which both the cover element 26 and the visor 24 are mounted pivotably on the prosthesis cosmetic 46, which is secured on the joint lower part 10. The proximal prosthesis part 40 is secured to the non-visible joint upper part 6 via an adapter 44. A distal prosthesis part 42, which in the present case is designed as a lower-leg tube, is arranged on the joint lower part 10.

FIG. 6 shows a bent or flexed state of the prosthesis 3 of the prosthesis system 2. In the maximally extended state, cover element 26 and visor 24 lie almost completely over each other. As flexion increases in the embodiment shown, visor 24 and cover element 26 initially move equally. This is because the cover element 26 is connected to the joint upper part 6 via the non-visible coupling element 28, and the cover element 26 is coupled to the visor 24 via a likewise non-visible driver.

Starting from approximately a pivoting angle of 50°, cover element 26 and visor 24 no longer cover the joint lower part 10 and the prosthesis cosmetic 46 ventrally, with the result that a gap forms as the flexion increases. The mechanics of the joint protection device 16 are preferably such that, starting from a pivoting angle of approximately 75°, the visor 24 remains stationary, i.e. does not pivot any farther with respect to the joint lower part 10 or the prosthesis cosmetic 46. Starting from this pivoting angle, only the cover element 26 continues to be pivoted, such that visor 24 and cover element 26 fold apart. This state is shown in FIG. 6. The pivoting angle here is more than 90°.

LIST OF REFERENCE SIGNS 2 prosthesis system
3 prosthesis
4 prosthesis joint
6 joint upper part
8 pyramid adapter
10 joint lower part
12 projection
14 carrier
16 joint protection device
18 structure
20 connection element
22 attachment element
24 visor
26 cover element
28 coupling element
30 portion
32 contact face
34 damping device
36 joint
38 gap
40 proximal prosthesis part
42 distal prosthesis part
44 adapter
46 prosthesis cosmetic
S pivot axis

The invention claimed is:

1. A prosthesis system having a prosthesis, which has two prosthesis parts connected to each other pivotably about a joint axis via a prosthesis joint with a joint upper part and a joint lower part, and having a cover element which at least partially covers a gap between the two prosthesis parts or between one prosthesis part and the joint lower part, wherein the cover element is mounted pivotably about a pivot axis on a prosthesis part, on a component of a prosthesis cosmetic secured to a prosthesis part or joint part, or on the prosthesis joint, wherein the cover element is coupled to the joint upper part of the prosthesis joint via at least one coupling element in a form-fitting and/or force-fitting manner, such that a pivoting movement of the prosthesis parts about the joint axis leads to a simultaneous pivoting movement of the cover element about the pivot axis, wherein the cover element is part of a multi-part joint protection device which is secured on the prosthesis joint, on one of the prosthesis parts or on the prosthesis cosmetic in a form-fitting and/or force-fitting manner and has a visor on which the cover element is mounted pivotably about the pivot axis, wherein the visor is secured on a carrier, on the prosthesis joint, on one of the prosthesis parts or on the prosthesis cosmetic so as to be pivotable about a pivot axis, the pivot axes of the visor and of the cover element coincide, wherein the visor and the cover element are additionally coupled to each other via at least one driver, and wherein the at least one coupling element is latched or clamped onto the joint upper part.

2. The prosthesis system of claim 1, wherein the joint protection device has a carrier on which the cover element and/or the visor is secured.

3. The prosthesis system of claim 1, wherein the cover element, the visor or a carrier has form-fit and/or force-fit elements via which the joint protection device is secured on the prosthesis joint, on one of the prosthesis parts or on the prosthesis cosmetic.

4. The prosthesis system of claim 1, wherein the joint protection device has a clasp-shaped design and is secured via a snap-fit connection, on the prosthesis joint, on one of the prosthesis parts or on the prosthesis cosmetic.

5. The prosthesis system of claim 1, wherein the joint protection device is secured releasably on the prosthesis joint, on one of the prosthesis parts or on the prosthesis cosmetic.

6. The prosthesis system of claim 1, wherein the visor and/or a carrier at least partially project over the gap between the two prosthesis parts.

7. The prosthesis system of claim 1, wherein, by the coupling of the visor and of the cover element during a flexion about the prosthesis joint, the gap is covered over a greater range than would be possible by means of the visor or cover element alone.

8. The prosthesis system of claim 1, wherein the pivot axis of the cover element and the joint axis of the prosthesis joint coincide.

9. The prosthesis system of claim 1, wherein the at least one coupling element is designed in one piece with the cover element in the form of a web, a clasp or a clip.

10. A prosthesis system comprising:
a prosthesis with two prosthesis parts pivotably connected to each other about a joint axis via a prosthesis joint, the joint including a joint upper part and a joint lower part; and
a cover element which at least partially covers a gap between the two prosthesis parts;
wherein the cover element is mounted pivotably about a pivot axis on a prosthesis part, on a component of a prosthesis cosmetic secured to a prosthesis part or joint part, or on the prosthesis joint, wherein the cover element is coupled to the joint upper part of the prosthesis joint via at least one coupling element in a form-fitting and/or force-fitting manner, such that a pivoting movement of the prosthesis parts about the joint axis leads to a simultaneous pivoting movement of the cover element about the pivot axis; and
wherein the cover element is part of a multi-part joint protection device which further comprises a visor on which the cover element is mounted pivotably about the pivot axis, wherein the visor is secured on a carrier, on the prosthesis joint, on one of the prosthesis parts or on the prosthesis cosmetic so as to be pivotable about a pivot axis, the pivot axes of the visor and of the cover element coincide, wherein the visor and the cover element are additionally coupled to each other via at least one driver, and wherein the at least one coupling element is latched or clamped onto the joint upper part.

11. The prosthesis system of claim 10, wherein the cover element, the visor or a carrier has form-fit and/or force-fit elements via which the joint protection device is secured on the prosthesis joint, on one of the prosthesis parts, or on the prosthesis cosmetic.

12. The prosthesis system of claim 10, wherein the joint protection device has a clasp-shaped design and is secured via a snap-fit connection on the prosthesis joint, on one of the prosthesis parts, or on the prosthesis cosmetic.

13. The prosthesis system of claim 10, wherein the joint protection device is secured releasably on the prosthesis joint, on one of the prosthesis parts, or on the prosthesis cosmetic.

* * * * *